United States Patent [19]

Hytönen

[11] Patent Number: 5,644,054
[45] Date of Patent: Jul. 1, 1997

[54] PROCESS FOR PREPARING DILTIAZEM

[75] Inventor: Martti Hytönen, Espoo, Finland

[73] Assignee: Orion-Yhtyma Oy Fermion, Espoo, Finland

[21] Appl. No.: 601,182

[22] Filed: Feb. 14, 1996

[30] Foreign Application Priority Data

Feb. 17, 1995 [FI] Finland .................................. 950719

[51] Int. Cl.$^6$ ...................... C07D 281/00; C07D 283/00; C07D 285/00
[52] U.S. Cl. ............................................................ 540/491
[58] Field of Search ............................................ 540/491

[56] References Cited

U.S. PATENT DOCUMENTS

| | | | |
|---|---|---|---|
| 3,582,257 | 6/1971 | Kugita et al. | 540/491 |
| 4,416,819 | 11/1983 | Nagao et al. | 540/491 |
| 4,438,035 | 3/1984 | Gaino et al. | 540/491 |
| 4,908,469 | 3/1990 | Martin | 540/491 |
| 5,514,589 | 5/1996 | Kanerva et al. | 435/280 |

FOREIGN PATENT DOCUMENTS

| | | | |
|---|---|---|---|
| 0081234 | 9/1985 | European Pat. Off. | 540/491 |
| 0353032 | 2/1992 | European Pat. Off. | 540/491 |
| 0594101 | 4/1994 | European Pat. Off. | 540/491 |
| WO02/10485 | 6/1992 | WIPO | 540/491 |

OTHER PUBLICATIONS

"Sodium Hydride—DMSO Mixture Explodes", *Chem. Eng. News*, 44(15), 48 (1966).

*Chemical Abstracts*, vol. 115, 1991, pp. 969 and 970, Abstract 232305, "Process for Preparing Benzothiazepine Derivatives", Rudolf Kubela et al., Abstract of Canadian Patent No. 1,284,321, granted May 21, 1991.

*Primary Examiner*—Robert T. Bond
*Attorney, Agent, or Firm*—Burns, Doane, Swecker & Mathis, L.L.P.

[57] ABSTRACT

A process is provided for preparing cis-(+)-hydroxy-5-[2-(dimethylamine)ethyl]-2,3-dihydro-2-(4-methoxyphenyl)-benzothiazepin-4(5H)-one that is a useful intermediate in the preparation of diltiazem. It has been found that the requisite N-alkylation reaction proceeds rapidly and with an excellent yield when the solvent is a mixture of toluene and N-methylpyrrolidin-2-one and the base is finely-divided sodium carbonate under anhydrous conditions. Such diltiazem commonly is used in the treatment of angina pectoris.

8 Claims, No Drawings

5,644,054

PROCESS FOR PREPARING DILTIAZEM

The present invention relates to a process for preparing cis-(+)-hydroxy-5-[2-(dimethylamino)ethyl]-2,3-dihydro-2-(4-methoxyphenyl)-benzothiazepin-4(5H)-one having the structure (I);

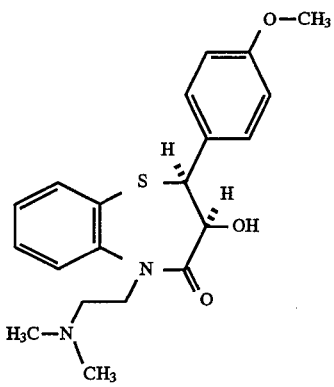

cis-(+)-hydroxy-5-[2-(dimethylamino)ethyl]-2,3-dihydro-2-(4-methoxyphenyl)-benzothiazepin-4(5H)-one is a useful intermediate in the preparation of diltiazem (II). Diltiazem is used currently in cardiovascular therapy, in particular in the treatment of angina pectoris.

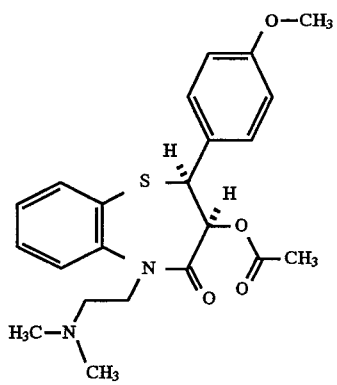

The preparation of diltiazem is described in patent U.S. Pat. No. 3,582,257, wherein the initial material used is cis-(+)-3-hydroxy-2-(4-methoxyphenyl)-2,3-dihydro-1,5-benzothiazepin-4(5H)-one (III).

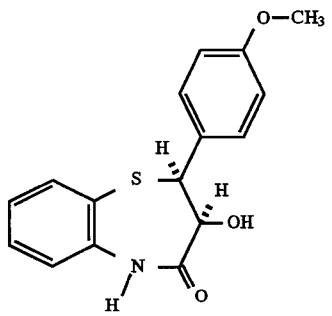

In the process described in the said patent, this compound reacts with 2-chloroethyldimethylamine (IV), forming the intermediate (I).

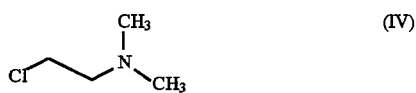

Dimethyl sulfoxide, toluene, xylene, and dioxane are described as possible solvents in this N-alkylation reaction. The base used in the reaction described in U.S. Pat. No. 3,562,257 is metallic sodium, sodium amide or sodium hydride. According to the patent, in particular dimethyl sulfoxide together with sodium hydride is especially well suited for this reaction. In connection with this reaction there is an evident risk of explosion (Chem. Eng. News, 44 (15), 48 (1966)) and, furthermore, dimethyl sulfoxide is difficult to regenerate, since it dissolves completely in water and its boiling point is high.

Patent EP 81234 describes an improved N-alkylation process, by which the disadvantages of the method according to the above-mentioned patent are avoided. In this process, compound (III) reacts with compound (IV), thereby forming compound (I). The reaction is carried out in the presence of potassium hydroxide in acetone or in the presence of potassium carbonate in a solvent which has been selected from among acetone, a lower alkyl acetate, a mixture of water and acetone, or a mixture of a lower alkyl acetate and water. However, when applied on an industrial scale, this process has severe disadvantages. In all of the processes described in the examples, the product is crystallized out, after a plurality of treatment steps, as its hydrochloride from ethanol in order that a sufficiently pure intermediate should be obtained. When acetone is used as the solvent, the after-treatment is complicated, since acetone is completely miscible with water and conventional removal of the salts cannot be carried out using water. The solvent must first be replaced with, for example, toluene, which is further, after the washing out of the salts, replaced with ethanol in order that the product could be crystallized and thereby freed of impurities. In all of the examples described in the patent, solvent is used in the alkylation reaction in an 8- to 10-fold amount in milliliters per one gram of the initial material to be alkylated. In the description section of the patent, the amount of solvent is limited to 5- to 15-fold in proportion to the initial material. On the basis of our laboratory experiments, those examples according to the patent in which the solvent is acetone or ethyl acetate and the base is potassium carbonate do not work repeatably. The reaction time in the examples of the patent varies from three hours in Example 2 to 30 hours in Example 7. If the time required by the reaction, the amount of solvent used in the reaction, and the cumbersome and complicated after-treatment are taken into consideration, these processes require a great deal of production capacity, working hours, and energy. Furthermore, ethylacetate hydrolyzes in alkaline conditions, and therefore its regeneration for reuse is problematic.

In U.S. Pat. No. 3,562,257, the alkylation of intermediate (III) takes place by the use of a base form of compound (IV), as also in patent application EP 594101, in which the N-alkylation reaction is carried out in toluene with sodium carbonate serving as the base.

This reaction is also described in patent application WO 92/10485, in which the solvent is toluene together with an auxiliary solvent, dimethyl formamide or N-methylpyrrolidin-2-one and water, and the base is potassium carbonate. However, the reaction requires the use of a phase transfer catalyst.

We have observed, surprisingly, that in the process according to the present invention the N-alkylation reaction proceeds rapidly and with an excellent yield when the solvent is a mixture of toluene and N-methylpyrrolidin-2-one and the base is finely-divided sodium carbonate. Toluene is needed in an amount only four-fold in proportion to the initial material. The water formed in the reaction is removed from the mixture by water separation. The reaction time is ½ –7 h depending on the temperature at which the reaction is performed. N-methyl-pyrrolidin-2-one is needed for dissolving the 2-chloroethyldimethylamine and for ensuring rapid proceeding of the reaction, in an amount of 0.5 grams per one gram of the initial material. The treatment after the reaction is decisively easier, since the salts can be washed out of the reaction mixture simply by adding water to the reaction mixture and by separating the layers. This procedure is possible, since toluene separates from water, contrary to acetone. It is also advantageous that the intermediate (I) obtained as the product is very pure, and no separate crystallization is needed; it is possible, after the separation of the water layer, to continue directly from intermediate (I) by distilling out the toluene for reuse and by then allowing the distillation residue to react with an acetic acid anhydride to form diltiazem, without a solvent.

The process according to the invention is characterized in that a compound according to Formula III

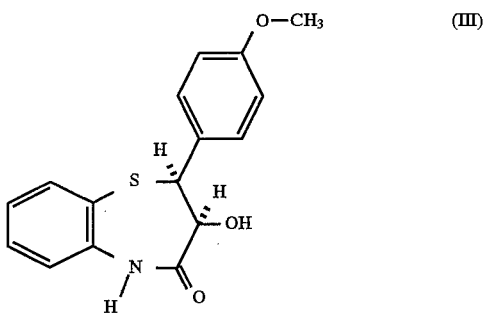

is allowed to react with a compound according to Formula (IV)

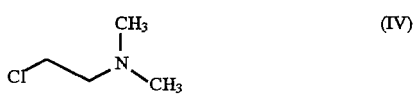

in a mixture of toluene and N-methylpyrrolidin-2-one in the presence of finely-divided sodium carbonate, whereby the desired intermediate product (I) is obtained

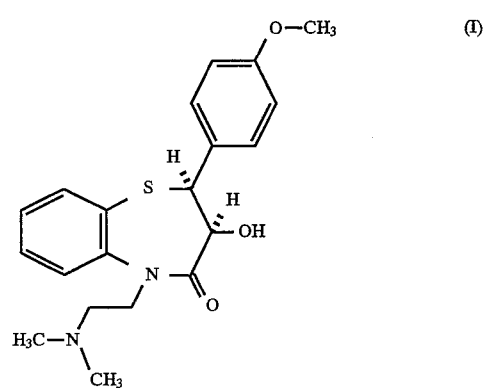

from which diltiazem (II) can be prepared directly by allowing the intermediate (I) to react, after the removal of the solvent, directly with an acetic acid anhydride.

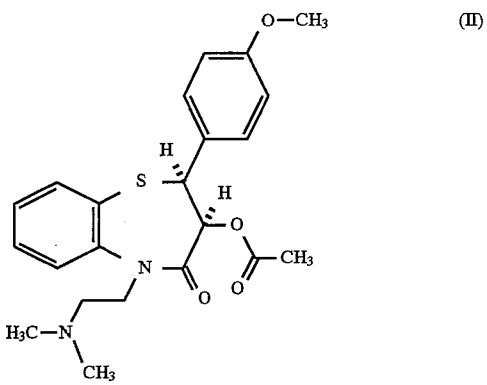

When compound (I) is prepared by the process according to the invention, compound (III) is allowed to react with compound (IV) in a mixture of N-methylpyrrolidin-2-one and toluene, which contains toluene in an amount of 50–95%, preferably 88%, and N-methyl-pyrrolidin-2-one in an amount of 5–50 5, preferably 12%, in the presence of finely-divided sodium carbonate having a particle size of 2–30 µm, preferably 8 µm, at a temperature of 80°–120° C., preferably 115° C., the reaction time being ½–7 h, most preferably 1 h.

The solvent of the N-alkylation reaction can be removed by distillation, and the distillation residue is allowed to react with acetic acid anhydride, without a solvent, to form diltiazem (II), from which the corresponding hydrochloride salt can further be prepared by a known method.

The process according to the invention does not require a separate unit operation for releasing the 2-chloroethyldimethylamine hydrochloride, in contrast to patent application EP 594101, in which this carcinogenic and highly toxic substance is released as a free base from its hydrochloride salt in a separate reactor before the actual performing of the N-alkylation reaction. In this latter case the said compound is extracted, after pH adjustment, into toluene from water, in which a portion of this toxic and highly water-soluble chlorinated amine will inevitably remain and cause considerable problems of waste treatment. In the process according to our invention, only the necessary amount of amine is batched as its hydrochloride directly into the reaction vessel. In the process according to patent application EP 594101, this carcinogenic substance is needed in an amount almost 70% more per one kilo of the initial material than in the process according to the present invention, and likewise sodium carbonate is also needed in an amount approximately 60% more per one kilo of the initial material. Furthermore, the process according to the present invention requires 45% less toluene. Thus the process according to the invention is, from the viewpoints of economy, capacity requirement and environmental protection, superior to the process mentioned in the foregoing.

In the process according to patent application WO 92/10485, toluene is needed in an amount 125% greater than in the process according to the invention, and furthermore, toxic 2-chloroethyldimethylamine hydrochloride is needed in an amount 15% greater. This process presupposes the use of an expensive phase transfer catalyst.

The following examples will illustrate the invention:

EXAMPLE 1

A mixture containing 96 g of cis-(+)-(4-methoxyphenyl)-3-hydroxy-2,3-dihydro-1,5-benzothiazepin-4(5H)-one, 52.8 g of 2-chloroethyldimethylamine hydrochloride, 90 g of finely-divided sodium carbonate, 384 ml of toluene, and 48 ml of N-methyl-pyrrolidin-2-one is heated, with water separation, to +115° C., and the mixture is stirred at that temperature for 1 h, whereafter the mixture is cooled to 40° C., and thereafter 240 ml of water is added to it and the layers are separated. The water layer is rejected. The product is in the toluene layer, which is washed once more with water. The process is continued by distilling out the toluene for reuse and by adding acetic acid anhydride to the distillation residue. After the treatment with acetic acid anhydride the product is extracted into toluene, from which it is crystallized out by adding a solution of ethanol and HCl. The product (I) of the alkylation reaction was not isolated, but the precise yield was determined. After the distillation out of toluene, 121.2 g of intermediate was left. From this, a 2-gram sample was weighed with precision, and this sample was purified by MPLC chromatography. The yield of pure product was 1.825 g (93.2%). The purity of the intermediate was checked by means of NMR spectra.

EXAMPLE 2

A mixture containing 32 g of cis-(+)-(4-methoxyphenyl)-3-hydroxy-2,3-dihydro-1,5-benzothiazepin-4(5H)-one, 17.6 g of 2-chloroethyldimethylamine hydrochloride, 30 g of finely-divided sodium carbonate, 128 ml of toluene, and 16 ml of N-methylpyrrolidin-2-one is heated under a vacuum of −0.42 bar to +93° C., whereupon the mixture boils, with water separation. Thereafter the vacuum is switched off, the mixture is cooled to +40° C. and is stirred at that temperature for 3 h, 84 ml of water is added, and the layers are separated. The water layer is rejected. The product is in the toluene layer, which is washed once more with water. The process is continued as in Example 1. The yield of the reaction was determined in the same manner as in Example 1, by weighing out from the evaporation residue, which was 40.73 g, precisely 2 grams for MPLC purification. The yield of pure intermediate after chromatographic purification was 1.827 g (94.1%). The purity of the intermediate was checked by means of NMR spectra.

I claim:

1. A process for preparing diltiazem according to Formula (II),

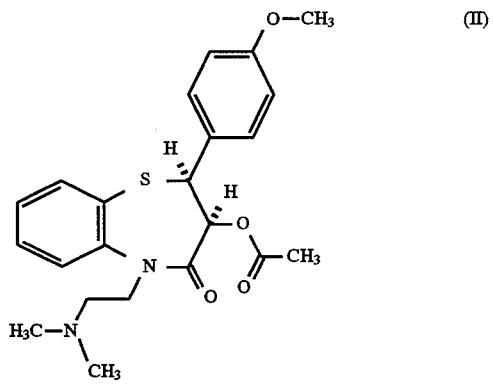

characterized in that a compound according to Formula (III)

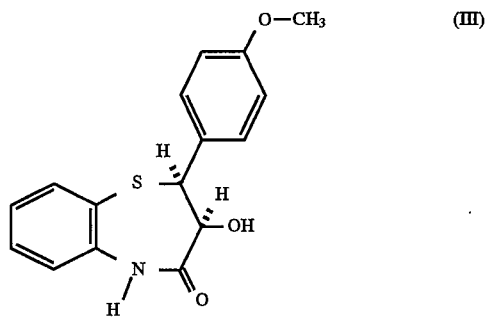

is allowed to react with a compound according to Formula (IV)

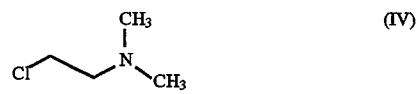

in a mixture of toluene and N-methylpyrrolidin-2-one in the presence of finely-divided sodium carbonate in anhydrous conditions to cis-(+)-hydroxy-5-[2(dimethylamino)ethyl]-2,3-dihydro-2-(4-methoxyphenyl)-benzothiazepin-4(5H)-one according to Formula (I),

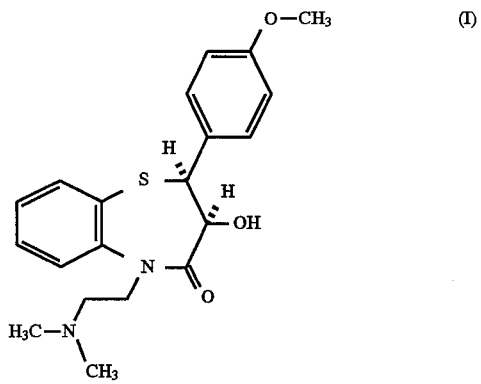

the solvents are removed by distallation after a water wash of the reaction mixture and the separation of the water layer, and the distallation residue is allowed to react with acetic acid anhydride to form diltiazem (II).

2. A process according to claim 1, characterized in that the mixture of toluene and N-methylpyrrolidin-2-one contains toluene 50–95% and N-methylpyrrolidin-2-one 5–50%.

3. A process according to claim 1, characterized in that the finely-divided sodium carbonate has a particle size of 2–30 μm.

4. A process according to claim 1, characterized in that the reaction temperature is 80°–120° C.

5. A process according to claim 2, characterized in that the finely-divided sodium carbonate has a particle size of 2–30 μm.

6. A process according to claim 2, characterized in that the reaction temperature is 80°–120° C.

7. A process according to claim 3, characterized in that the reaction temperature is 80°–120° C.

8. A process according to claim 5, characterized in that the reaction temperature is 80°–120° C.

* * * * *